United States Patent [19]

Goldberg

[11] Patent Number: 4,787,884

[45] Date of Patent: Nov. 29, 1988

[54] URETERAL STENT GUIDEWIRE SYSTEM

[75] Inventor: Jay Goldberg, Northbrook, Ill.

[73] Assignee: Medical Engineering Corporation, Racine, Wis.

[21] Appl. No.: 91,976

[22] Filed: Sep. 1, 1987

[51] Int. Cl.$^4$ .............................................. A61M 25/00
[52] U.S. Cl. ....................................... 604/8; 604/170; 128/657
[58] Field of Search ...................................... 604/8–10, 604/170; 128/656–658, 772

[56] References Cited

U.S. PATENT DOCUMENTS

| | | | |
|---|---|---|---|
| 229,663 | 7/1980 | Pfarre | 128/341 |
| 243,396 | 6/1981 | Pfarre | 128/341 |
| 3,631,848 | 1/1972 | Muller | 128/2.05 R |
| 3,757,768 | 9/1973 | Kline | 128/2 M |
| 4,212,304 | 7/1980 | Finney | 128/349 R |
| 4,307,723 | 12/1981 | Finney | 128/349 R |
| 4,531,933 | 7/1985 | Norton et al. | 604/8 |
| 4,610,657 | 9/1986 | Densow | 604/8 |
| 4,616,652 | 10/1986 | Simpson | 128/772 |
| 4,671,795 | 6/1987 | Mulchin | 604/281 |

OTHER PUBLICATIONS

Radiology (U.S.A.) vol. 136, No. 1, pp. 230 and 231 (Jul. 1980).

Primary Examiner—Dalton L. Truluck
Attorney, Agent, or Firm—Quarles & Brady

[57] ABSTRACT

A dual wire guidewire system for inserting a ureteral stent with a proximal end with a reduced opening into the ureter of a patient comprises an elongated tubular pusher wire, an elongated guidewire and a retaining member. The pusher wire is open at both ends and sized to fit in the lumen of the stent. The leading end of the pusher wire has a diameter larger than the reduced opening in the stent. The guidewire is sized to fit within the lumen of pusher wire and has a leading end which is smaller in diameter than the reduced opening in the stent. The retaining member keeps the leading end of the guidewire from leaving the lumen of the pusher wire. When an obstruction is encountered in the ureter, the retaining member is disengaged and the leading end of the guidewire is passed through the reduced opening and maneuvered past the obstruction. The pusher wire and stent then can be advanced over the guidewire past the obstruction.

5 Claims, 2 Drawing Sheets

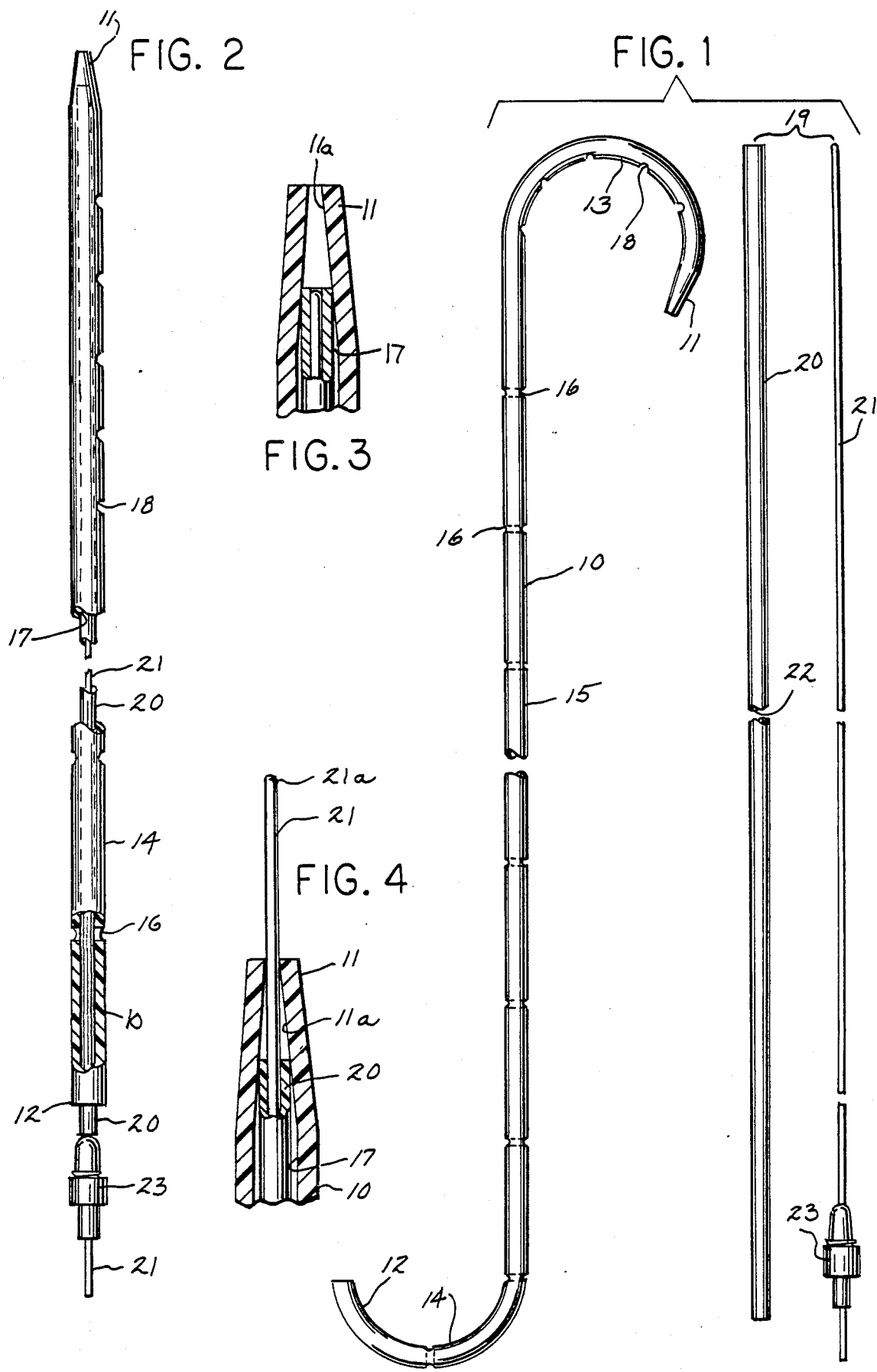

URETERAL STENT GUIDEWIRE SYSTEM

RELATED CASE

This application is related to the commonly owned, copending U.S. patent application Ser. No. 893,381 filed August 5, 1986, now U.S. Pat. No. 4,713,049.

FIELD OF THE INVENTION

The present invention relates generally to ureteral stents. More particularly, it relates to a dual wire guidewire system which can be used to maneuver a stent past obstructions.

BACKGROUND OF THE INVENTION

Indwelling ureteral catheter stents or drainage tubes have been used to bypass ureteral obstructions or ureterovaginal fistulas and to achieve and to maintain urinary drainage. In the past, stents made of straight lengths of open end tubing have been used for this purpose and have provided good drainage for sustained periods of time. However, the use of such tubing has not been completely satisfactory. For example, in some instances, the tubing has migrated and in others it has been expelled.

Various attempts have been made to produce stents which do not have the problems which accompany the use of such tubing. For example, stents have been designed which are closed at one end to facilitate passage into a body passage and which have at the other end a flange to make upward migration of the stent less likely. Another approach has been to provide the body of the stent with sharply pointed barbs which are designed to prevent downward migration and expulsion. However, such barbs increase the diameter of the stent making it more difficult to insert and in some instances can cause the stent to migrate outside the bladder.

In Finney U.S. Pat. No. 4,212,304 issued July 15, 1979 and Finney U.S. Pat. No. 4,307,723 issued Dec. 29, 1981, ureteral stents are disclosed which have hooks at each end and which are surprisingly effective in preventing migration and expulsion. The patented stents are widely accepted because they can be easily introduced both endoscopically and during open surgery. However, like most other commercially available stents it is difficult to maneuver them past obstructions in the ureter.

In Densow U.S. Pat. No. 4,610,657 a stent is disclosed which has a hook at each end, a lumen and a reduced opening at the proximal end. The guidewire system disclosed for use with the stent comprises two separate guidewires. One of the wires is the pusher wire. It is smaller in diameter than the lumen of the stent but has a proximal end which is larger than the reduced opening at the proximal end; it is used to push the stent in place when no obstructions are encountered. The other wire is used when an obstruction is encountered. It is smaller in diameter than the first wire and the reduced opening in the stent. When an obstruction is encountered the stent and the pusher wire are withdrawn and the pusher wire is removed. The smaller diameter wire is inserted in the lumen of the stent and the stent and wire reinserted; the leading end of the smaller wire is then advanced out the reduced opening in the proximal end and maneuvered past the obstruction. The stent is then run over the guidewire past the obstruction. Once the leading end of the stent is past the obstruction, the stent is pushed into place with the pusher wire or a stent pusher.

It would be advantageous to have a guidewire system that could be used to either advance a stent in the normal fashion or to guide it past an obstruction without having to withdraw the stent from the patient to replace the guidewire or having to withdraw the guidewire from the stent before it is in place.

SUMMARY OF THE INVENTION

It is an object of the present invention to disclose a dual wire guidewire system which can be used to either place a stent with an open proximal end in place in the normal manner or to maneuver the stent past an obstruction in the ureter without having to withdraw the stent or the guidewire.

It is another object to disclose a method of bypassing an obstruction in the ureter using the dual wire guidewire system of the present invention.

The dual wire guidewire system of the present invention comprises a pusher wire comprising an elongated tubular member; a small diameter guidewire which fits within the lumen of the tubular member; and, retaining means for keeping the guidewire in the pusher wire until it is needed. The guidewire system of the present invention is for use with a stent with a reduced opening at the proximal end, such as that disclosed in the Densow patent, supra.

The pusher wire of the present invention is an elongated, tubular member which has a leading end with an outer diameter which is small enough to move freely in the lumen of the stent having a reduced opening at the proximal end but which is too large to pass through the reduced opening. When the guidewire is in place in the pusher wire, the combination is rigid enough to straighten the hooks of the stent and to push the stent in place. The pusher wire is of sufficient length to allow it and the guidewire to be used endoscopically to place the stent in the lower calyx or renal pelvis of a patient.

The guidewire which fits within and moves freely within the lumen of the pusher wire has a leading end which is small enough in diameter to pass through the reduced opening in the proximal end of the stent. The guidewire is longer than the pusher wire which permits it to be extended out of the pusher wire and the open end of the stent and maneuvered past an obstruction if one is encountered in the ureter.

The retaining means is normally locked or clamped on the portion of the guidewire adjacent the distal end of the pusher wire; it keeps the guidewire inside the pusher wire until an obstruction is encountered. At that time, the retaining means is disengaged and moved adjacent the distal end of the guidewire so that the leading end of the guidewire can be advanced out of the proximal opening in the stent past the obstruction. The retaining means can be locked or clamped on the distal end of the guidewire so that it can be used as a handle.

The stent is normally inserted in the ureter by placing the proximal end of the dual wire guidewire system into an opening at the distal end of the stent. The guidewire system is advanced in the stent until the leading ends of the pusher wire and guidewire have reached the proximal end of the stent. Because of the rigidity of the pusher wire and guidewire combination, the hooks of the stent are straightened in the process. Next, the stent and proximal portion of the dual guidewire system are passed through a cystoscope into the ureter. The stent is then pushed into place utilizing the distal portion of the pusher wire and guidewire combination which is outside of the stent.

In the event that an obstruction in the ureter is encountered which prevents the stent from being inserted in the renal pelvis or lower calyx using the pusher wire and guidewire combination in the normal manner, the retaining means is disengaged from the distal end of the pusher wire and moved adjacent to the distal end of the longer guidewire. The leading end of the guidewire can then be advanced out of the lumen of the pusher wire and out of the proximal opening in the stent and maneuvered past the obstruction. Once the leading end of the guidewire is past the obstruction and in the desired location, the stent and pusher wire are advanced over the guidewire past the obstruction until the stent is positioned in the desired location. The dual guidewire system is then separated from the stent and withdrawn leaving the stent in place.

The dual wire guidewire system of the present invention will usually be marketed in a kit containing an open end stent and the guidewire system including a pusher wire, a guidewire and retaining means. A conventional tubular stent pusher such as that described in the Densow patent, supra., can also be included to facilitate separating the stent from the guidewire system.

The above stated and other objects and advantages of the invention will be apparent from the description which follows:

DESCRIPTION OF THE DRAWINGS

FIG. 1 is an elevational view of the preferred embodiment of the kit which includes a stent and the guidewire system of the present invention;

FIG. 2 is an elevational view showing the guidewire system in the stent with the hooks of the stent straightened;

FIG. 3 is an enlarged sectional view of the proximal end of the stent of FIG. 2, showing the leading end of the pusher wire seated against the reduced opening of the proximal end of the stent;

FIG. 4 is a view similar to FIG. 3 showing the leading end of the pusher wire seated against the tapered wall of the opening in the proximal end of the stent and the leading end of the guidewire extending out of the reduced proximal opening of the stent; and, FIG. 5 is an enlarged sectional view of the retaining means mounted on the guidewire.

DESCRIPTION OF THE PREFERRED EMBODIMENT

Figure 5:
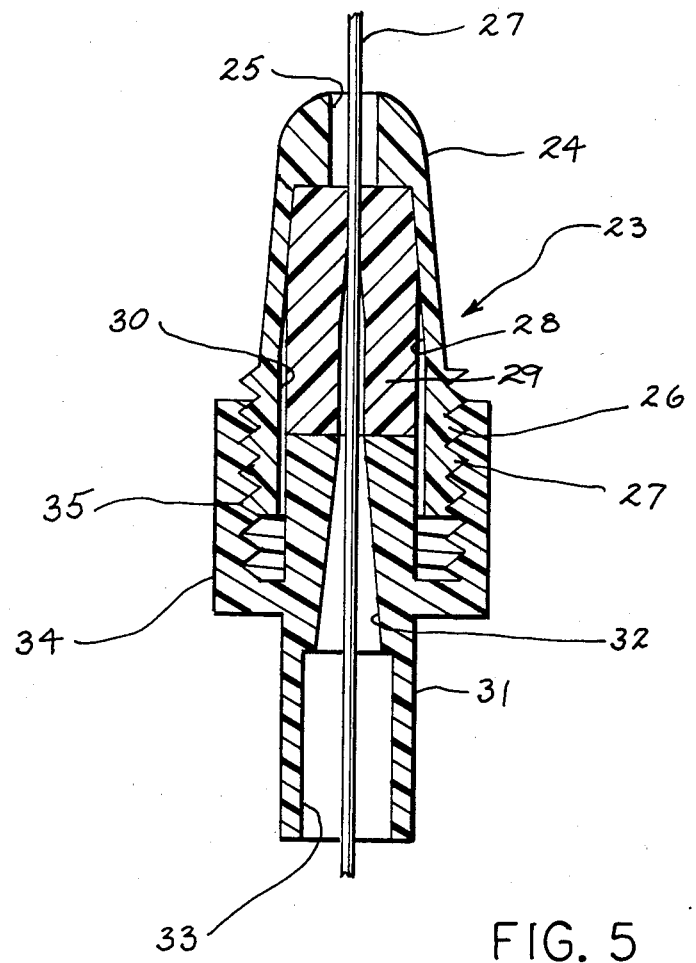

In the preferred embodiment shown in FIG. 1, the kit includes a stent 10 which is an elongated tubular member having a proximal end 11 and a distal end 12. Portions adjacent each of the ends 11 and 12 of the stent 10 are formed and set in the shape of gently curved hooks 13 and 14. Both the proximal end 11 and the distal end 12 as shown are open. The opening at the distal end 12 is of substantially the same diameter as the lumen of the stent, but the opening 11a at the proximal end is of smaller diameter (seen best in FIGS. 3 and 4). In some cases, it may be preferred to supply the stent 10 with the distal end 12 closed and an opening (not shown) in the side wall which is sized to receive the guidewire system.

The two gently formed opposed hooks 13, 14 of the stent 10 prevent it from migrating either upwardly or downwardly once it is in place. The hooks 13 and 14 preferably extend in opposite directions so that when the stent 10 is used as an indwelling ureteral stent the proximal end 11 can hook into the lower calyx or renal pelvis while the distal end 12 curves out into the bladder. This design also prevents the tip of the stent from impinging directly into the bladder mucosa thereby decreasing discomfort and inflammation.

The stent 10 includes a relatively straight intermediate section 15 which extends between the proximal hook 13 and the distal hook 14.

Referring now to FIGS. 1 to 4, it can be seen that the stent 10 has radial drainage passages 16 which connect the lumen 17 of the stent 10 to the outside and to permit inside/outside drainage. The drainage passages 16 are located about 5 centimeters apart on both sides of the straight section 15. The passages 16 of both sides are preferably aligned. There are similar openings 18 in the inside wall of the proximal hook 13.

Referring to FIG. 1, there can be seen the novel dual wire guidewire system 19 of the present invention. As seen therein, the guidewire system comprises a relatively large diameter pusher wire 20, which is sized to fit in the lumen 17 of the stent 10; a longer, smaller diameter guidewire 21 which is sized to fit within the lumen 22 of the pusher wire 20; and, the retaining means 23.

The retaining means 23, as seen best in FIG. 5, consists of a chuck 24 which has an open nose 25 and a base 26 with an external thread 27. The chuck 24 also has a bore 28 in which there is an insert 29 which has a bore 30 which is about the same diameter as the exterior of the guidewire 21. The insert 29 is of a deformable material. The open nose 25 of the chuck (seen only in FIG. 5) is sized to receive the outside diameter of the pusher wire 20. The retaining means 23 also includes a chuck tightening body 31 which has a bore 32 which is tapered so that it is narrower at the top and it expands to a Luer type adapter 33 at the bottom. The chuck tightening body 31 has adjacent to and projecting past its top an integral collar 34 with an internal thread 35 that mates with the thread 27 of the chuck 24.

The retaining means 23 is locked or clamped on the guidewire 21 by screwing the chuck tightening body 31 on the chuck 24. As the two pieces are tightened the deformable insert 29 is twisted and/or compressed to deform the bore 30 and lock the retaining means 23 onto the guidewire 21. The retaining means 23 can be disengaged by untightening the chuck tightening body 31 whereupon the retaining means 23 can be moved to the end of the guidewire 21 and reclamped there so it can be used as a handle.

When normal endoscopic insertion is employed, the guidewire system comprising the relatively large diameter pusher wire 20 and the relatively small diameter guidewire 21 is assembled with the guidewire 21 in the pusher wire 20 and the retaining means 23 engaged as seen in FIG. 2. The proximal end of the combination is introduced into the lumen 17 of the stent 10 via the open distal end 12. The guidewire system 19 is then advanced until the proximal hook 13 is straightened as seen in FIG. 2.

Once the stent 10 is properly positioned, the guidewire system 19 can be removed leaving the stent in place. A stent pusher can be used to keep the stent in place while the guidewire system is being separated.

When an obstruction in the ureter is encountered that cannot be bypassed by the stent 10 using the normal method of introduction, the retaining means 23 is disengaged and moved to the distal end of the guidewire 21 where it is reengaged for use as a handle. The leading end 21a of the guidewire 21 is then advanced out of the reduced opening 11a of the stent 10 (as seen in FIG. 4) and maneuvered past the obstruction in the ureter. When it is known that the leading end 21a is safely past the obstruction, the pusher wire 20 and the stent 10 are moved over the guidewire 21 past the obstruction. The entire guidewire system 19 can then be withdrawn. If desired, only the guidewire may be withdrawn and fluid introduced into the patient via the pusher wire lumen 22 and stent lumen 17.

When it is desired to replace an indwelling stent of the type shown, the stent is first cystoscopically visualized and then a foreign body forceps or a retractable type stone basket (neither shown) is advanced through the cystoscope and used to retract the stent 10 until the distal end 12 can be reached and used to withdraw the stent from the patient.

The stent 10 is made of a suitable flexible material which is soft and stiff enough for the intended purpose and which preferably contains a radiopaque material. The stent may be supplied in various sizes and lengths. The listed length of the stent 10 is the length of the section 15 and does not include the hooked ends 13 and 14. To assist the urologist, the section 15 may be provided with marks every 5 cm and a longitudinal stripe which shows which direction the straightened hooks will assume when relaxed.

The ureteral stent 10 of the present invention is preferably made of a thermoplastic material which has a durometer between about 70 Shore 'A' and about 55 Shore 'D' to which barium sulfate has been added as the radiopaque agent. The stents should be soft enough not to cause undue discomfort to the patient and stiff enough to bypass obstructions in the ureter. Other plastic materials such as silicone rubber which possess the desired properties and resist encrustation with urine salts can also be used.

The stent 10 is preferably formed by extruding a length of tubing of the desired size and durometer. The proximal end 11 of the tubing is then placed in a mold to form the internally tapered, reduced open end 11a. The length of tubing is then placed in a form to shape the hooks 13 and 14. The openings 16 and 18 may be formed at any step of the process by piercing the wall of the tubing with a flattened, sharpened hole cutter of the desired size or by use of a laser or any other conventional means.

The pusher wire 20 is a flexible, tubular member open at both ends. The preferred pusher wire has an OD of about 0.045 inches, and ID of about 0.035 inches.

The guidewire 21 is sized to fit within and is more rigid than the pusher wire 20; it may be formed of stainless steel wire. It has an OD of about 0.032 inches. The length of the guidewire 21 is sufficiently greater than that of the pusher wire 20 so that the leading end can be extended out from the lumen 22 of the pusher wire 20 past any obstruction that might be encountered.

The kit of the present invention will normally comprise a stent 10 and the guidewire system 19. The dual wire guidewire system 19 also may be sold separately without the stent 10.

In the preferred embodiment described and shown in the drawing, the proximal and distal end portions of the stent are both in the form of gently curved, closed hooks. However, it is to be understood that the term "hook" is intended to include other functionally equivalent shapes such as coils which prevent migration and do not increase the effective outer diameter of the stent, or complicate its method of introduction. It also should be understood that the guidewire system of the present invention may be used with other types of ureteral stents including adjustable length stents and stents with magnetically attractable distal ends.

It will be readily apparent to those skilled in the art that a number of modifications and changes can be made without departing from the spirit of the invention. Therefore, it is to be understood that the scope of the invention is not be limited by the foregoing description, but only by the claims.

I claim:

1. A dual wire guidewire system for use in inserting a ureteral stent having an open proximal end of reduced diameter into a patient, said guidewire system comprising an elongated, tubular pusher wire of generally uniform diameter having a lumen which is open at both ends; a relatively flexible guidewire, said guidewire being longer than the pusher wire and sized to fit in and move freely in the lumen of said pusher wire so that the leading edge of said guidewire can be advanced out of the lumen of the pusher wire; and retaining means for keeping the leading end of the guidewire within the lumen of the pusher wire, said retainer means comprising a chuck having a bore for receiving the guidewire and a chuck tightening means which can be tightened to deform the bore and lock the guidewire within the chuck of the retaining means.

2. A ureteral stent kit comprising an elongated flexible stent of substantially uniform outside surface throughout its length having a lumen and a reduced open proximal end and a dual wire guidewire system, said guidewire system comprising a pusher wire open at both ends, said pusher wire being sized to fit within the lumen of the stent and of larger diameter than the reduced open proximal end of the stent so that it can be used to push the stent into place; a guidewire, said guidewire being sized to freely move within the lumen of said pusher wire and having a leading end which is small enough to pass through the reduced open proximal end of the stent so that if an obstruction is encountered it can be bypassed by maneuvering the leading end of the guidewire past the obstruction and the stent can be advanced past the obstruction over said guidewire; and retaining means for keeping the leading end of the guidewire within the lumen of the pusher wire until an obstruction is encountered.

3. A kit for bypassing obstructions in the ureter with a ureteral stent, said kit comprising:
   (a) a ureteral stent comprising an elongated, relatively flexible, tubular member having at least one drainage opening extending through a wall thereof, said member having a lumen, an open proximal end of reduced diameter and at least one end set in the form of a hook;
   (b) a tubular pusher wire, said pusher wire being sized to fit and move within the lumen of said stent and having a central lumen, the leading end of said pusher wire being larger than the reduced open proximal end of the stent;
   (c) a guidewire, said guidewire being sized to both fit within and move freely in the lumen of said pusher wire so that when the pusher wire and guidewire are within the lumen of the stent they can be advanced to straighten both hooks; said guidewire having a leading end which is smaller in diameter than the reduced open proximal end of the stent so that if an obstruction in the ureter is encountered the leading end of the guidewire can be moved out of the pusher wire and the reduced opening of the stent and maneuvered past the obstruction so that both the stent and pusher can be advanced past the obstruction by moving them over the guidewire; and (d) retaining means for keeping the leading end of the guidewire inside the lumen of the pusher wire until an obstruction is encountered.

4. A kit of claim 3 in which the retaining means clamps onto the guidewire.

5. A method for inserting a ureteral stent in the ureter and for maneuvering the stent past any obstructions in the ureter which might be encountered, said method comprising:

(a) introducing into the ureter a ureteral stent comprising an elongated, flexible, tubular member having a lumen, said member having at least one drainage passage extending through a wall thereof connecting the lumen to the outside and a proximal end with a reduced opening; said stent having in the lumen thereof a dual wire guidewire system comprising a tubular, flexible pushed wire having a lumen open at both ends; a guidewire which is sized to fit within and move in the lumen of the pusher wire; and retaining means for retaining the leading end of the guidewire within the lumen of the pusher wire;

(b) advancing said stent and guidewire system in the patient until an obstruction in the ureter is encountered;

(c) then disengaging the retaining means and passing the leading end of said guidewire out through the reduced opening and maneuvering the leading end of the guidewire past the obstruction; and (d) then advancing the pusher wire and the stent over the guidewire and past the obstruction.

* * * * *